United States Patent
Brendel et al.

[19]

[11] Patent Number: 5,905,627
[45] Date of Patent: May 18, 1999

[54] INTERNALLY GROUNDED FEEDTHROUGH FILTER CAPACITOR

[75] Inventors: Richard L. Brendel, Carson City, Nev.; Robert A. Stevenson, Canyon Country, Calif.

[73] Assignee: Maxwell Energy Products, Inc., San Diego, Calif.

[21] Appl. No.: 08/926,238

[22] Filed: Sep. 10, 1997

[51] Int. Cl.[6] ..................................................... H01G 4/35
[52] U.S. Cl. ....................... 361/302; 361/303; 361/306.1; 361/309
[58] Field of Search ..................... 361/302, 303, 361/306.1, 306.2, 307, 309, 321.2, 328, 329, 330; 333/181, 182, 183, 184; 174/152 GM, 143

[56] References Cited

U.S. PATENT DOCUMENTS

| | | | |
|---|---|---|---|
| 2,756,375 | 7/1956 | Peck | 361/302 |
| 3,235,939 | 2/1966 | Rodriguez et al. | 29/25.42 |
| 3,538,464 | 11/1970 | Walsh | 361/302 |
| 3,920,888 | 11/1975 | Barr | 174/152 GM |
| 4,083,022 | 4/1978 | Nijman | 333/183 |
| 4,144,509 | 3/1979 | Boutros | 333/181 |
| 4,148,003 | 4/1979 | Colburn et al. | 333/181 |
| 4,152,540 | 5/1979 | Duncan et al. | 174/152 GM |
| 4,220,813 | 9/1980 | Kyle | 174/152 GM |
| 4,247,881 | 1/1981 | Coleman | 361/302 |
| 4,314,213 | 2/1982 | Wakino | 333/182 |
| 4,352,951 | 10/1982 | Kyle | 174/152 GM |
| 4,362,792 | 12/1982 | Bowsky et al. | 361/302 |
| 4,424,551 | 1/1984 | Stevenson et al. | 361/302 |
| 4,456,786 | 6/1984 | Kyle | 174/152 GM |
| 4,737,601 | 4/1988 | Gartzke | 174/152 GM |
| 4,741,710 | 5/1988 | Hogan et al. | 439/620 |
| 5,032,692 | 7/1991 | DeVolder | 174/52.3 |
| 5,070,605 | 12/1991 | Daglow et al. | 372/222 |
| 5,142,430 | 8/1992 | Anthony | 361/56 |
| 5,333,095 | 7/1994 | Stevenson et al. | 361/302 |
| 5,751,539 | 5/1998 | Stevenson et al. | 361/302 |

*Primary Examiner*—Kristine Kincaid
*Assistant Examiner*—Anthony Dinkins
*Attorney, Agent, or Firm*—Kelly Bauersfeld Lowry & Kelley, LLP

[57] ABSTRACT

An internally grounded ceramic feedthrough filter capacitor assembly provides for the shielding and decoupling of a conductive terminal pin or lead of the type used, for example, in an implantable medical device such as a cardiac pacemaker or cardioverter defibrillator against passage of external interference signals, such as those caused by digital cellular phones. The assembly includes a terminal pin subassembly having at least one terminal pin supported within a conductive ferrule by a hermetically sealed insulator structure. The ferrule is adapted for mounting onto a conductive substrate, such as a pacemaker housing, by welding or brazing to support the terminal pin subassembly for feedthrough passage to the housing interior. A ceramic feedthrough capacitor is mounted at an inboard side, with the capacitor electrode plate sets coupled respectively to a grounded lead and to the terminal pins(s) by conductive adhesive, soldering, brazing or the like. In preferred forms of the invention, multiple feedthrough filter capacitors are provided in a substantially coplanar array within a common base structure, with each capacitor in association with a respective terminal pin.

29 Claims, 7 Drawing Sheets

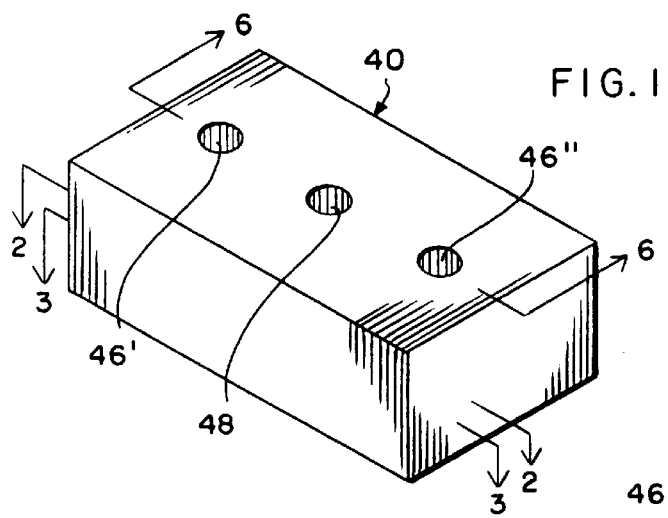
FIG. 1
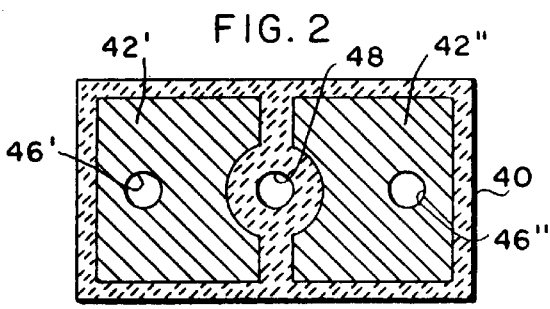
FIG. 2
FIG. 3
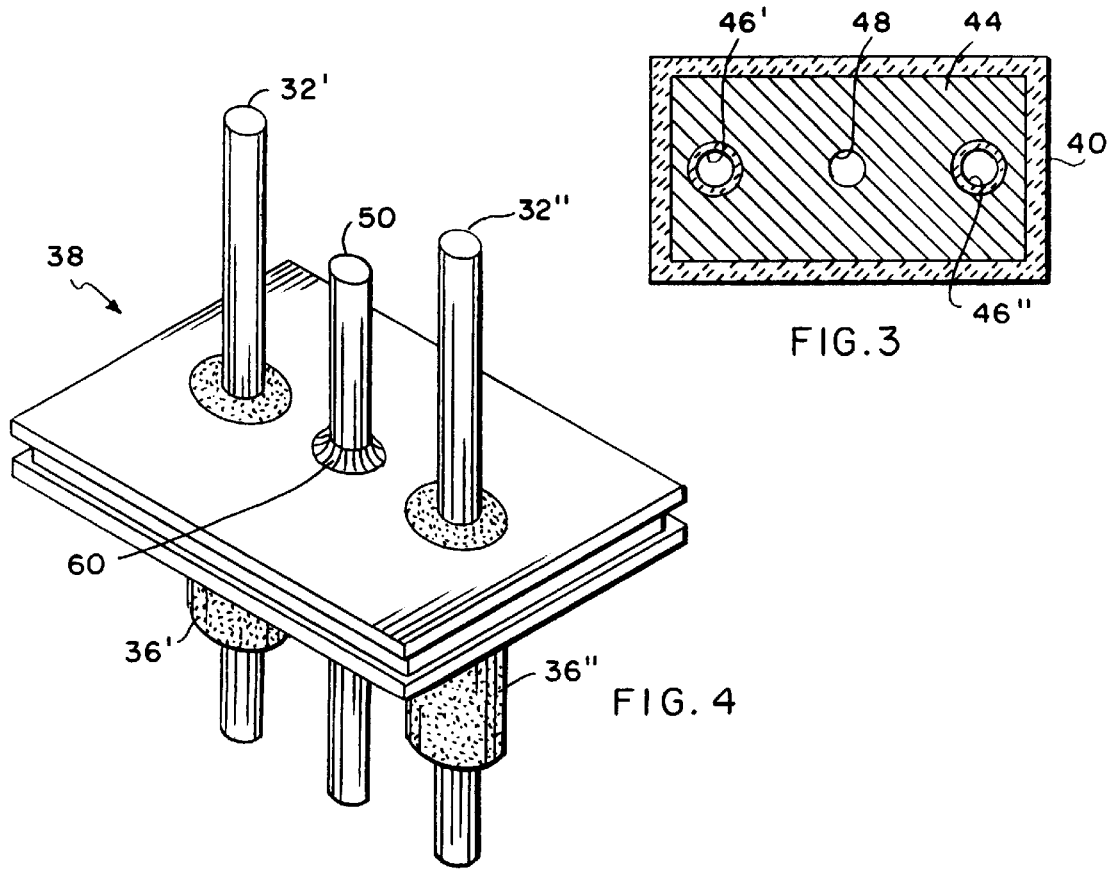
FIG. 4

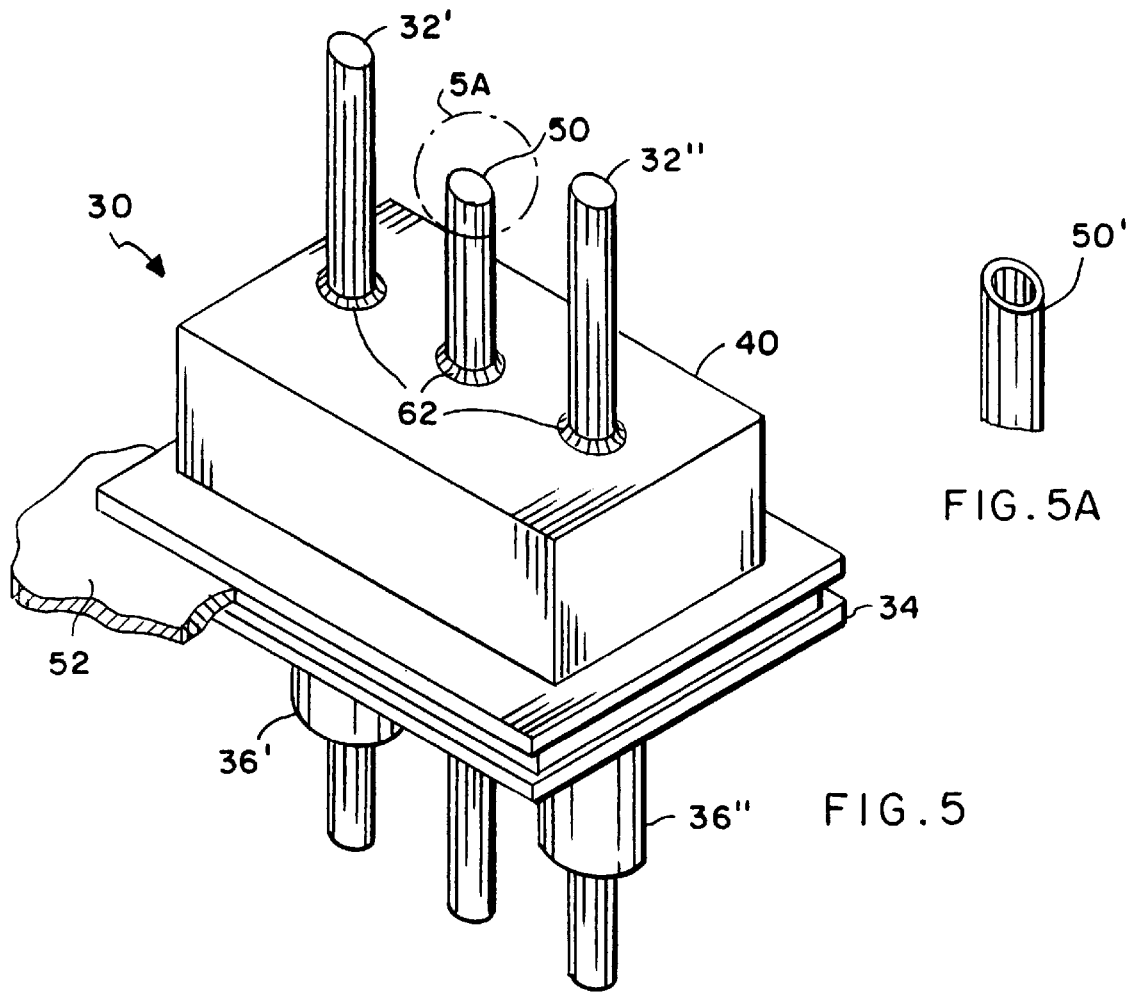
FIG. 5
FIG. 5A
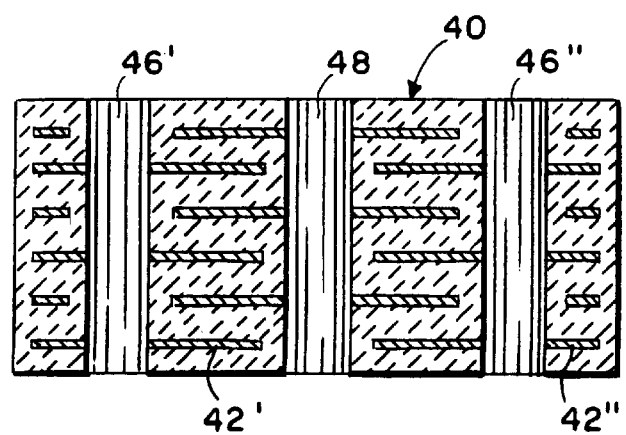
FIG. 6

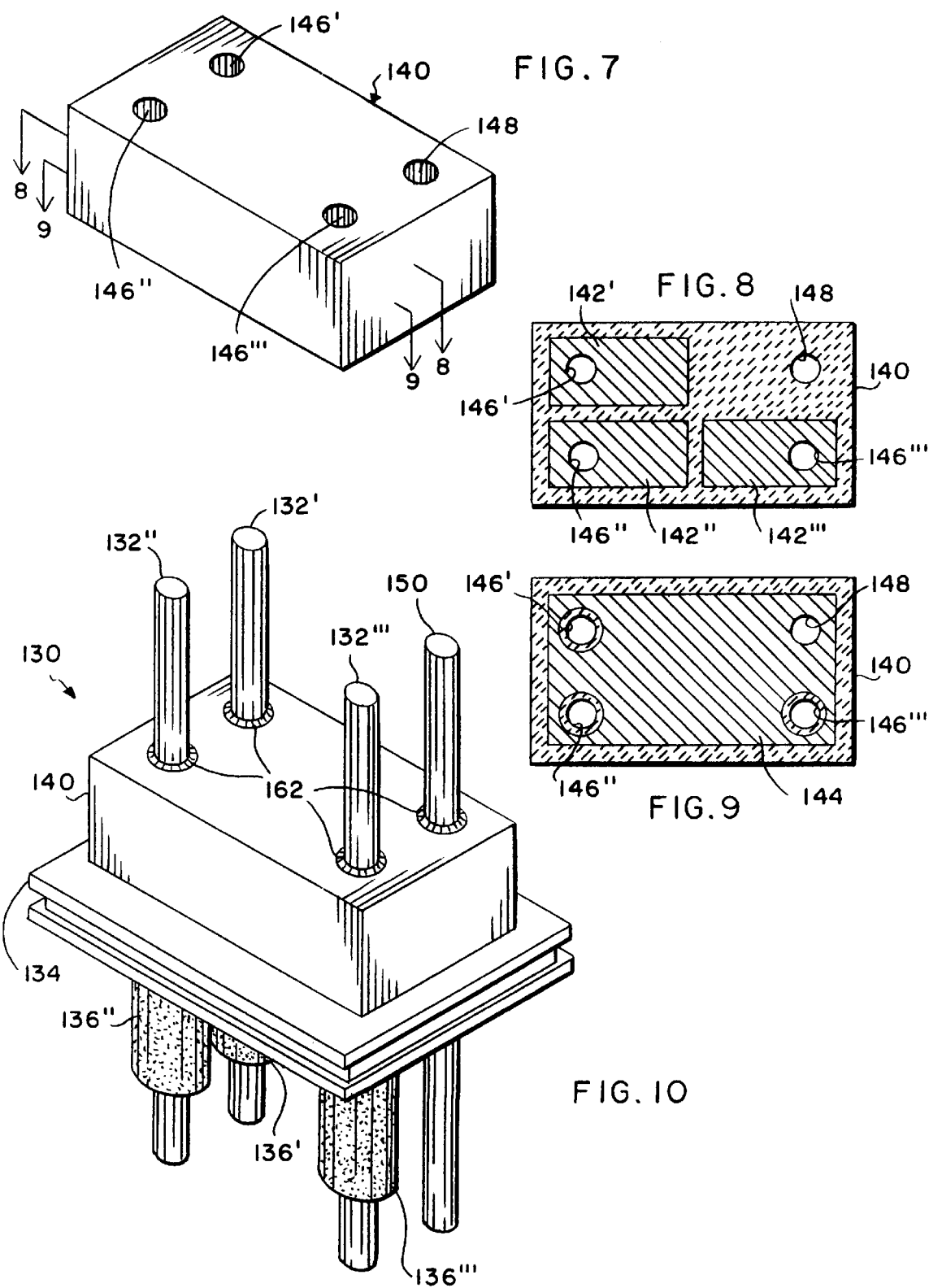

INTERNALLY GROUNDED FEEDTHROUGH FILTER CAPACITOR

BACKGROUND OF THE INVENTION

This invention relates generally to simplified feedthrough terminal pin subassemblies and related methods of construction, particularly of the type used in implantable medical devices such as cardiac pacemakers and the like, to decouple and shield undesirable electromagnetic interference (EMI) signals from the device. More specifically, this invention relates to a reduced cost and reduced mechanical stress hermetic feedthrough terminal pin and ceramic feedthrough capacitor assembly including one or more filter capacitors, and related installation method. It is adapted particularly for use in connecting a lead wire or electrode through a hermetically sealed housing to internal electronic components of the medical device while decoupling EMI against entry into the sealed housing. This invention is particularly designed for use in cardiac pacemakers (bradycardia devices), cardioverter defibrillators (tachycardia devices) and combined pacemaker defibrillator devices. This invention is also applicable to a wide range of other EMI filter applications, such as military or space electronic modules where it is desirable to preclude the entry of EMI into a sealed housing containing sensitive electronic circuitry.

Feedthrough terminal pin assemblies are generally well known in the art for connecting electrical signals through the housing or case of an electronic instrument. For example, in implantable medical devices such as cardiac pacemakers, defibrillators or the like, the terminal pin assembly comprises one or more conductive terminal pins supported by an insulator structure for feedthrough passage from the exterior to the interior of the medical device. Many different insulator structures and related mounting methods are known in the art for use in medical devices wherein the insulator structure also provides a hermetic seal to prevent entry of body fluids into the housing of the medical device. However, the feedthrough terminal pins are typically connected to one or more lead wires which effectively act as an antenna and thus tend to collect stray EMI signals for transmission into the interior of the medical device. In many prior art devices, the hermetic terminal pin assembly has been combined directly with a ceramic feedthrough filter capacitor to decouple interference signals to the housing of the medical device. A major market force within the medical implantable device industry has been to reduce cost of the implanted device (e.g. pacemaker or implantable cardioverter defibrillator). Medical insurance carriers, government healthcare programs (e.g. Medicare) and health maintenance organizations (HMOs) are placing additional competitive pressures on the manufacturers of such devices.

In a typical unipolar construction, as described in U.S. Pat. No. 5,333,095 (the contents of which are incorporated herein), a coaxial ceramic feedthrough filter capacitor used in a feedthrough assembly to suppress and decouple undesired interference or noise transmission along a terminal pin comprises a so-called discoidal capacitor having two sets of electrode plates embedded in spaced relation within an insulative dielectric substrate or base, formed typically as a ceramic monolithic structure. One set of the electrode plates is electrically connected at an inner diameter cylindrical surface of the discoidal capacitor structure to the conductive terminal pin utilized to pass the desired electrical signal or signals. The other or second set of electrode plates is coupled at an outer diameter surface of the discoidal capacitor to a cylindrical ferrule of conductive material, wherein the ferrule is electrically connected in turn to the conductive housing of the electronic device. The number and dielectric thickness spacing of the electrode plate sets varies in accordance with the capacitance value and the voltage rating of the discoidal capacitor. In operation, the discoidal capacitor permits passage of relatively low frequency electrical signals along the terminal pin, while shielding and decoupling/attenuating undesired interference signals of typically high frequency to the conductive housing. Feedthrough capacitors of this general type are available in unipolar (one,) bipolar (two), tripolar (three), quadpolar (four), pentapolar (five), hexpolar (six) and additional lead configurations. The feedthrough capacitors of this general type are commonly employed in implantable cardiac pacemakers and defibrillators and the like, wherein the pacemaker housing is constructed from a biocompatible metal, such as titanium alloy, which is electrically coupled to the feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function.

In the past, feedthrough filter capacitors for cardiac pacemakers and the like have typically been constructed by preassembly of the discoidal capacitor within a cylindrical terminal pin subassembly which includes the conductive pin and ferrule. More specifically, the terminal pin subassembly is prefabricated to include one or more conductive terminal pins supported within the conductive ferrule by means of a hermetically sealed insulator ring or bead. See for example, the subassemblies disclosed in U.S. Pat. Nos. 3,920,888; 4,152,540; 4,421,947; and 4,424,551. An improved design which has substantially improved the volumetric efficiency is based upon surface mounting of a ceramic feedthrough capacitor planar array structure to one outer surface of a hermetic terminal with similar connection to the conductive pins (see the subassemblies disclosed in U.S. Pat. No. 5,333,095). In all of the prior art described above, the outer feedthrough capacitor electrode plate sets are coupled in parallel together by a metallized layer which is either fired, sputtered or plated onto the ceramic capacitor. This metallized band, in turn, is coupled to the ferrule by conductive adhesive, soldering, brazing, or the like.

Although feedthrough filter capacitor assemblies of the type described above have performed in a generally satisfactory manner, the manufacture and installation of such filter capacitor assemblies has been relatively time consuming and therefore costly. For example, installation of the discoidal capacitor into the small annular space described by U.S. Pat. No. 4,424,551 between the terminal pin and ferrule can be a difficult and complex multi-step procedure to ensure formation of reliable, high quality electrical connections. The method taught by U.S. Pat. No. 4,424,551 (the contents of which are incorporated herein), teaches the injection of fluidic thermosetting conductive particles into first and second annular cavities (usually by centrifuge operations). As a consequence, this method also requires insulation of the interface between the capacitor structure and insulator, curing of the various thermosetting materials, and subsequent cleaning operations to remove excess conductive material. While the method taught by U.S. Pat. No. 5,333,095 is far simpler, a connection from the capacitor outside diameter and the conductive ferrule is still required.

A high integrity hermetic seal for medical implant applications is very critical to prevent the ingress of body fluids into the implanted device (e.g. pacemaker). Even a small leak rate of such body fluid penetration can, over a period of many years, build up and damage sensitive internal electronic components. This can cause catastrophic failure of the implanted device. The hermetic seal for medical implant (as well as space and military) applications is typically constructed of highly stable alumina ceramic or glass materials with very low bulk permeability. A helium fine leak test is typically used in conjunction with a sensitive detector to reject defective or cracked hermetic seals. This final product quality conformance test is typically of very short duration (a few seconds helium exposure). This short test exposure will readily detect a leak in a cracked or otherwise defective alumina ceramic or glass hermetic seal; however, it typically takes much longer for helium to penetrate through an epoxy or polyimide adjunct barrier (such polymer overcoating can mask the leak).

Withstanding the high temperature and thermal stresses associated with the welding of a hermetically sealed terminal with a premounted ceramic feedthrough capacitor is very difficult to achieve with the '551, '095 and other prior art designs. The electrical/mechanical connection to the outside perimeter or outside diameter of the feedthrough capacitor has a very high thermal conductivity as compared to air. The welding operation typically employed in the medical implant industry to install the filtered hermetic terminal into the ICD can involve a welding operation in very close proximity to this electrical/mechanical connection area. Accordingly, in the prior art the ceramic feedthrough capacitor is subjected to a dramatic temperature rise. This temperature rise produces mechanical stress in the capacitor due to the mismatch in thermal coefficients of expansion of the surrounding materials. In addition, in the prior art the capacitor lead connections must be of very high temperature materials to withstand the high peak temperatures reached during the welding operation (as much as 500° C.). A similar, but less severe, situation is applicable in military, space and commercial applications where similar prior art devices are soldered instead of welded by the user into a bulkhead or substrate. Many of these prior art devices employ a soldered connection to the outside perimeter or outside diameter of the feedthrough capacitor. Excessive installation soldering heat has been known to damage such prior art devices.

Accordingly, there is a need for a novel feedthrough filter capacitor assembly that addresses the drawbacks noted above in connection with the prior art. In particular, a novel capacitor assembly is needed that is subjected to far less temperature rise during the manufacture thereof by eliminating an outside perimeter or outside diameter electrical/mechanical connection. Such a design would allow the use of much lower temperature materials (such as standard solder) to achieve the capacitor inside diameter lead connections. Moreover, such an improvement would make the assembly relatively immune to the aforementioned stressful installation techniques. Moreover, a novel filter capacitor design is needed which is of simplified construction, utilizing a straightforward and uncomplicated feedthrough terminal pin subassembly, that can result in manufacturing cost reductions. Of course the new design must be capable of effectively filtering out undesirable electromagnetic interference (EMI) signals from the target device. The present invention fulfills these needs and provides other related advantages.

SUMMARY OF THE INVENTION

The present invention resides in an internally grounded ceramic. feedthrough filter capacitor assembly for shielding and decoupling of a conductive terminal pin or lead of the type used, for example, in an implantable medical device such as a cardiac pacemaker or cardioverter defibrillator, to prevent the passage of externally generated electromagnetic (EM) fields such as interference signals caused by digital cellular telephones. The feedthrough filter capacitor assembly is typically mounted upon a conductive substrate such as, for example, a conductive pacemaker housing. The assembly comprises, generally, at least one conductive terminal pin and means for mounting the terminal pin for passage through an opening formed in the conductive substrate with the terminal pin and the substrate in non-conductive relation. A feedthrough filter capacitor is provided which has first and second sets of electrode plates. The terminal pin extends through a first passageway through the feedthrough filter capacitor in conductive relation with the first set of electrode plates. A ground lead extends into a second passageway through the feedthrough filter capacitor and is conductively coupled to the second set of electrode plates and the conductive substrate.

The terminal pin mounting means comprises a conductive ferrule adapted for mounting onto the substrate in a position extending through the substrate opening, and insulator means for supporting the terminal pin from the ferrule in electrically insulated relation. The terminal pin, ferrule and insulator means comprises a prefabricated terminal pin subassembly.

Various embodiments of the invention are disclosed herein which illustrate that the feedthrough filter capacitor may be asymmetrical as well as symmetrical about the ground lead, that the terminal pin may include a wire bond pad at one end thereof, and that the ground lead may comprise a solid pin or a hollow gas back-fill tubelet, etc. The ground lead may comprise a nail-head lead having one end that abuts a portion of the conductive ferrule and, if desired, the nail head lead may extend from the conductive ferrule through and beyond the feedthrough filter capacitor to provide a ground pin. Alternatively, the ground lead may comprise a ground pin that extends through the conductive ferrule and feedthrough filter capacitor. In this case, means may be provided for hermetically sealing passage of the terminal pin and the ground pin through the conductive substrate.

Utilization of an internally grounded feedthrough filter capacitor as disclosed herein permits use of a capacitor having non-metallized exterior surfaces. A ferrite bead disc inductor may also be utilized in connection with the feedthrough filter capacitor to enhance the filtering performance and characteristics of the capacitor assembly.

In one preferred form of the invention for medical implant applications, the feedthrough filter capacitor assembly includes a terminal pin subassembly having at least one terminal pin supported within a conductive ferrule by a hermetically sealed insulator structure. The ferrule is adapted for mounting into a conductive pacemaker housing by welding or brazing to support the terminal pin subassembly for feedthrough passage to the interior of the housing. A ceramic feedthrough capacitor is mounted at an inboard side of the terminal pin subassembly, with capacitor electrode plate sets coupled respectively to a ground pin and to active terminal pin(s) by conductive adhesive, soldering, brazing or the like. In one preferred form, multiple feedthrough filter capacitors are provided in a substantially coplanar array within a common base structure, with each capacitor in association with a respective terminal pin.

The internally grounded monolithic feedthrough filter capacitors utilized in the assemblies of the present invention advantageously eliminate the need to conductively couple a metallized exterior surface of the capacitor to a portion of the conductive substrate or ferrule, as was required in the prior art.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view of a monolithic, ceramic, internally grounded bipolar feedthrough filter capacitor embodying aspects of the present invention;

FIG. 2 is a sectional view of the bipolar feedthrough filter capacitor taken generally along the line 2—2 of FIG. 1, illustrating two sets of metallic electrode plates silk-screened onto ceramic plates;

FIG. 3 is a sectional view taken generally along the line 3—3 of FIG. 1, illustrating a ground plane provided within the bipolar feedthrough filter capacitor;

FIG. 4 illustrates a terminal pin subassembly having a pair of conductive terminal pins and a ground pin mounted to a conductive ferrule;

FIG. 5 is a perspective view of the bipolar feedthrough filter capacitor of FIG. 1 mounted to the terminal pin subassembly of FIG. 4;

FIG. 5A is an enlarged fragmented perspective view illustrating an alternative type of ground pin comprising a hollow gas back-fill tubelet, that may be substituted for the solid ground pin of FIG. 5;

FIG. 6 is an enlarged sectional view of the feedthrough filter capacitor of FIG. 1, taken generally along the line 6—6 of FIG. 1;

FIG. 7 is a perspective view of an asymmetrical tripolar internally grounded feedthrough filter capacitor embodying aspects of the present invention;

FIG. 8 is a horizontal section taken generally along the line 8—8 of FIG. 7, illustrating three sets of conductive plates embedded within the tripolar feedthrough filter capacitor of FIG. 7;

FIG. 9 is a horizontal sectional view taken generally along the line 9—9 of FIG. 7, illustrating a ground plane within the tripolar feedthrough filter capacitor;

FIG. 10 is a perspective view illustrating the tripolar internally grounded feedthrough filter capacitor associated with a corresponding terminal pin subassembly;

DETAILED DESCRIPTION OF THE PREFERRED EMBODIMENTS

Figure 14:
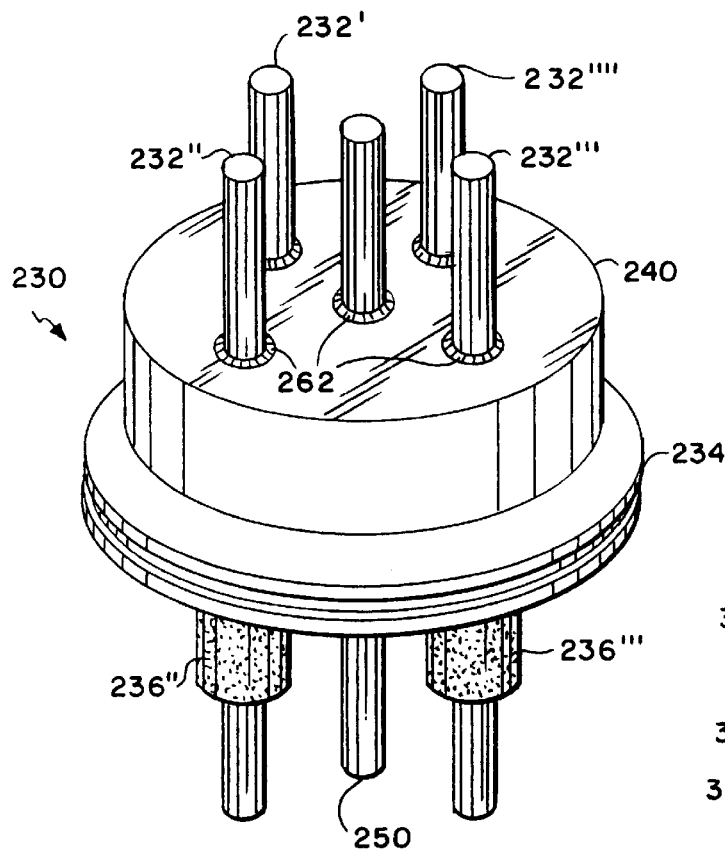
FIG. 14 is a perspective view of the internally grounded quadpolar feedthrough filter capacitor of FIG. 11 assembled to a corresponding terminal pin subassembly.
Figure 16:
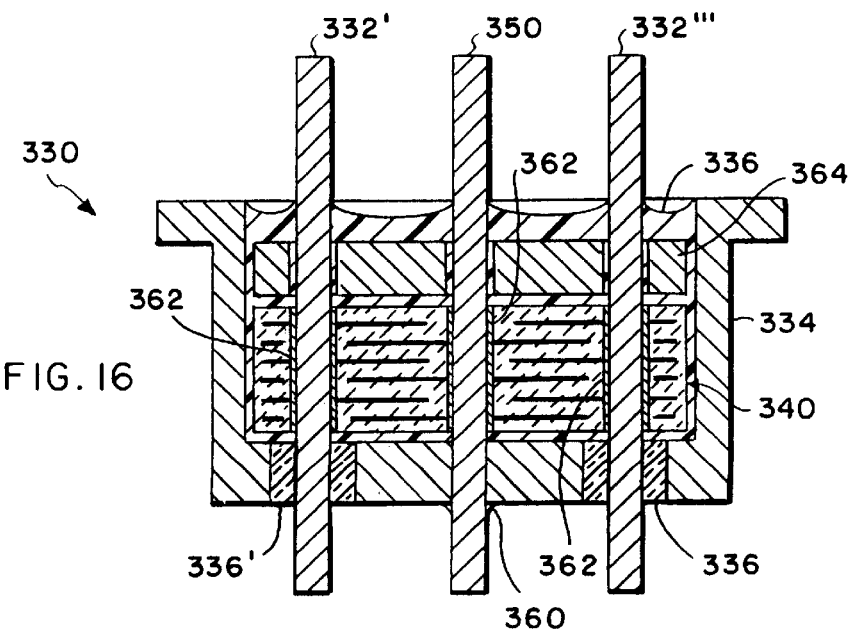
FIG. 16 is an elevational sectional view of an alternative quadpolar (discoidal) feedthrough filter capacitor that includes the features of the embodiment of FIGS. 11–14, wherein the quadpolar feedthrough filter capacitor is housed with a receptacle-like conductive ferrule that is, in turn, conductively connected to a conductive substrate, and further illustrating the placement of a ferrite bead disc inductor over the quadpolar feedthrough filter capacitor to enhance filtering characteristics of the assembly.
Figure 18:
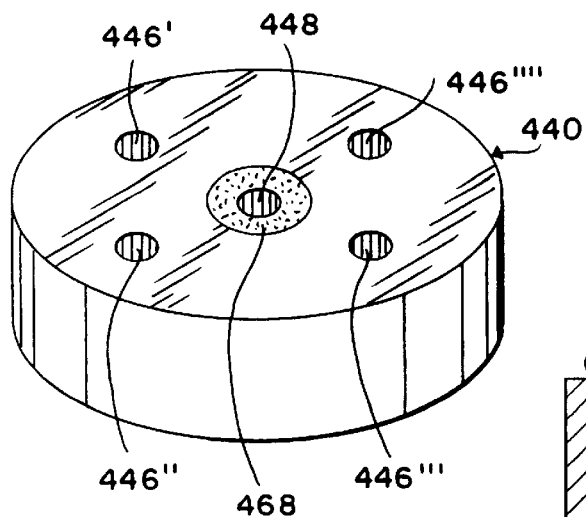
FIG. 18 illustrates another type of internally grounded quadpolar (discoidal) feedthrough filter capacitor similar to that illustrated in FIG. 11.
Figure 19:
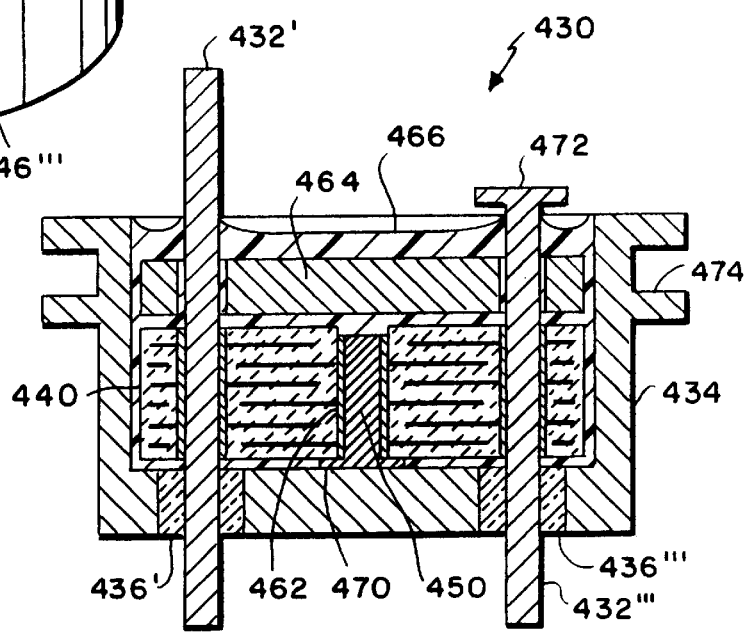
FIG. 19 is an elevational sectional view similar to that shown in FIG. 16, wherein a nail-head (or welded, or swaged or the like) lead is utilized instead of a ground pin to ground the capacitor to the conductive ferrule, a wire bond pad is provided one of the conductive terminals, and also a laser weld H flange is provided for attachment to a conductive housing, such as the can halves of an implantable defibrillator.
Figure 20:
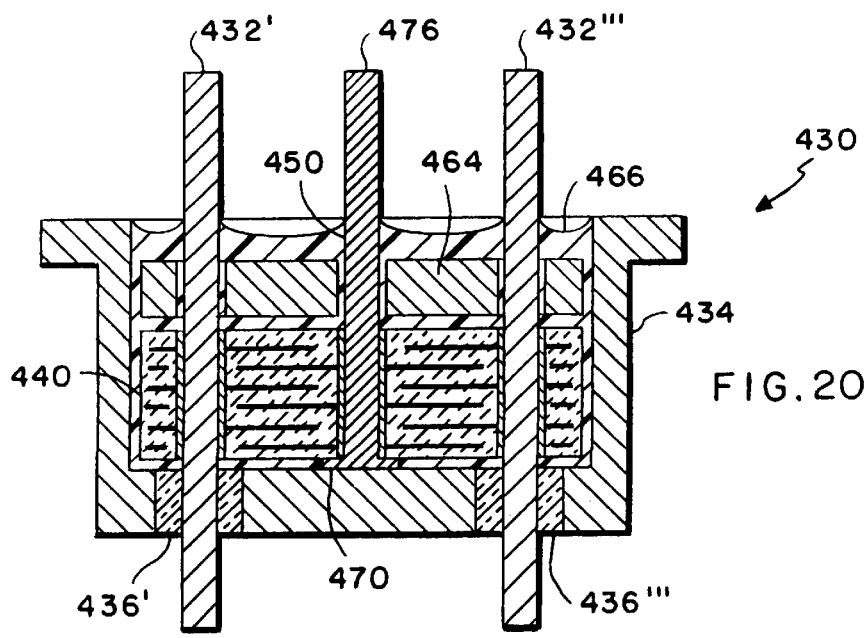
FIG. 20 is an elevational sectional view similar to that of FIG. 19, and illustrating the provision of a ground pin provided by the nail-head lead.
Figure 21:
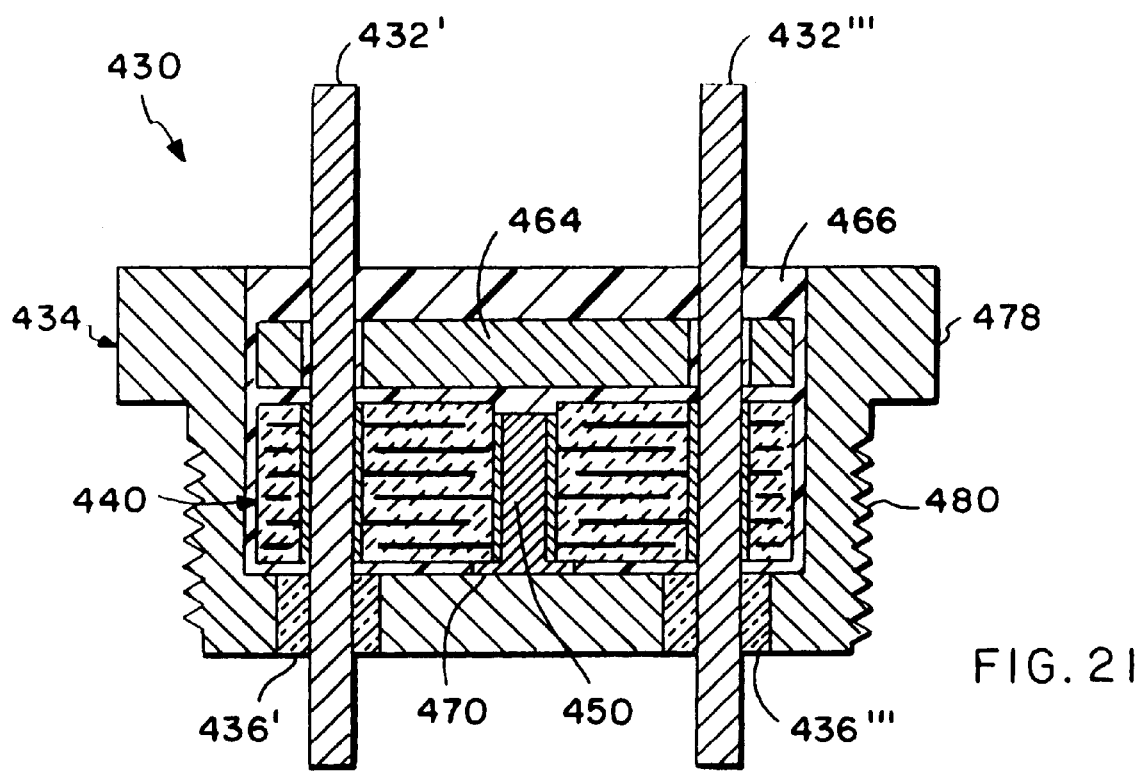
FIG. 21 is an elevational sectional view similar to that shown in FIGS. 19 and 20, illustrating the inclusion of a hex head and mounting threads on an external surface of the conductive ferrule, to facilitate mounting of the conductive ferrule to a conductive substrate.

As shown in the drawings for purposes of illustration, the present invention is concerned with a novel internally grounded feedthrough filter capacitor assembly generally designated in FIG. 5 by the reference number 30, in FIG. 10 by the reference number 130, in FIG. 14 by the reference number 230, in FIG. 16 by the reference number 330, and in FIGS. 19–21 by the reference number 430. In the following description, functionally equivalent elements of the various embodiments will share the same reference number in increments of 100. The improved feedthrough filter capacitor assemblies 30-430 comprise, generally, at least one conductive terminal pin 32-432 and a conductive ferrule 34-434 through which the terminal pin passes in non-conductive relation. An insulator 36-436 supports each conductive terminal pin 32-432 from the conductive ferrule 34-434 in electrically insulated relation, and the assembly of the terminal pin(s), the conductive ferrule and the insulator(s) comprises a terminal pin subassembly 38. The feedthrough filter capacitor assemblies 30-430 further include a feedthrough filter capacitor 40-440 that has first and second sets of electrode plates 42-442 and 44-444. A first passageway 46-446 is provided through the feedthrough filter capacitor 40-440 through which the terminal pin 32-432 extends in conductive relation with the first set of electrode plates 42-442. The feedthrough filter capacitor 40-440 further includes a second passageway 48-448 into which a ground lead 50-450 extends. The ground lead is conductively coupled to the second set of electrode plates 44-444 and the conductive ferrule 34-434. Typically, the conductive ferrule 34-434 is conductively mounted to a conductive substrate 52 that may comprise, for example, the housing for an implantable medical device.

The invention as described herein eliminates the need for external conductive connections between the capacitor and a ground by connecting the internal ground plates to a ground pin, tubelet, or similar ground lead structure. This is a particularly convenient and cost effective approach for certain implantable cardioverter defibrillators (ICDs) that already employ a grounded terminal pin in order to use the titanium housing of the implanted ICD as one of the cardiac electrodes. Another convenient method to attach the internal ground plates is to use the hollow fill tubelet 50' (FIG. 5A) of certain implantable devices which is used to evacuate and backfill with inert gasses. As there is no external electrical connection, the need for external capacitor metallization around the capacitor perimeter or outside diameter has also been eliminated. This not only reduces expensive metallization firing or plating operations, but also eliminates the joining of materials which are not perfectly matched in thermal coefficient of expansion.

In other similar applications (non-medical), it is very typical to carry the ground or floating circuit ground connection through a connector (such connectors are widely used in space, military and telecommunications applications). Connection of the internally grounded capacitor electrode plates would be accomplished in a similar manner to that described above for medical implant devices.

In accordance with the present invention and with reference to FIGS. 1–6, the feedthrough filter capacitor 40 comprises a monolithic, ceramic internally grounded bipolar feedthrough filter capacitor having three passageways extending therethrough. The outer two passageways are configured to receive therethrough respective conductive terminal pins 32' and 32", and the internal diameter of the first passageways 46 are metallized to form a conductive link between the first sets of electrode plates 42' and 42". As is well understood in the art, the first sets of electrode plates 42 are typically silk-screened onto ceramic plates forming the feedthrough filter capacitor 40. These plates 42 are surrounded by an insulative ceramic material that, for purposes of the present invention, need not be metallized on its exterior surfaces.

Similarly, a second set of electrode plates 44 is provided within the feedthrough filter capacitor 40. The inner diameter of the central or second passageway 48 through the feedthrough filter capacitor 40 is also metallized to conductively connect the second set of electrode plates 44, which comprise the ground plane of the feedthrough filter capacitor 40. The second passageway 48 is configured to receive therethrough the ground lead 50 which, in this particular embodiment, comprises a ground pin.

With reference to FIG. 4, the terminal pin subassembly 38 comprises a plate-like conductive ferrule 34 having three apertures therethrough that correspond to the three passageways through the feedthrough filter capacitor 40. The conductive terminal pins 32' and 32" are supported through the outer apertures by means of an insulator 36' and 36" (which also may be hermetic), and the ground pin 50 is supported within the central aperture by a suitable conductor 60 such as solder, an electrically conductive thermosetting material or welding/brazing.

The feedthrough filter capacitor 40 is placed adjacent to the non-body fluid side of the conductive ferrule 34 and a conductive attachment is effected between the metallized inner diameter of the first and second passageways 46 and 48 through the feedthrough filter capacitor 40 and the respective terminal pins 32 and ground lead 50. As was the case described above in connection with the attachment of the ground lead 50 to the conductive ferrule 34, the conductive connection 62 between the terminal pins 32 and the ground lead 50 with the feedthrough filter capacitor 40 may be effected by any suitable means such as a solder or an electrically conductive thermosetting material or brazing. The result is the feedthrough filter capacitor assembly 30 illustrated in FIG. 5 which may then be attached to the conductive substrate 52.

Internally grounding a ceramic feedthrough capacitor through a ground lead has heretofore not been considered because such construction increases the electrical impedance (particularly inductance) of the connection between the internal capacitor ground electrode plates and the conductive ferrule. This results in a reduction of the high frequency attenuation of the filter capacitor structure. However, with cost becoming an increasingly important issue, the internal grounding method becomes an attractive alternative. This tradeoff is further enhanced by the natural tendency body tissues have to absorb (attenuate) RF energy at higher frequencies. The tendency to increase the impedance can be minimized by symmetrical placement of the ground pin as illustrated in the embodiments of FIGS. 5, 14, 16 and 19–22. However, non-symmetrical arrangements as illustrated in the embodiment of FIG. 10 still provide a high (and acceptable) degree of attenuation.

Another way of stating this is that the reduction of filter attenuation by the internal ground at high frequency tends to be offset by the natural tendency of the human body to absorb (or attenuate) high frequency RF energy. The efficacy of the internal ground was recently demonstrated by laboratory testing (in vitro) performed by the Federal Food and Drug Administration Center for Devices and Radiological health (FDA-CDRH). A fully functional implantable cardioverter defibrillator (ICD) was fitted with the asymmetrical internally grounded feedthrough capacitor assembly 130 illustrated in FIG. 10 (worst case from an impedance standpoint) and then placed within a standardized saline tank to simulate body fluids. The instrumental ICD was immune to the EM fields produced by various model cellular phones. This is a result similar to previous testing which demonstrated that cardiac pacemakers fitted with EMI filters described by either the '551 or '095 patents were also immune to the EM fields produced by digital cellular phones (this previous testing also demonstrated that when these filters were removed, the cardiac pacemakers were susceptible to the EM fields with instances of complete inhibition of the pacemaker output). Inhibition of the pacemaker output pulse, is of course, a potentially life threatening situation for patients who depend upon the implanted device output pulse for each and every heartbeat.

With reference now specifically to FIGS. 7–10, the components of the feedthrough filter capacitor assembly 130 are illustrated. In this embodiment, the feedthrough filter capacitor 140 comprises an asymmetrical tripolar internally grounded feedthrough filter capacitor. The general construction of this particular embodiment of the invention is quite similar to that described above in connection with the assembly of FIGS. 1–6. The feedthrough filter capacitor 140 includes three passageways 146', 146" and 146''', each having metallized inner diameters for receiving therethrough respective conductive terminal pins 132' and 132" and 132'''. These conductive terminal pins 132 are conductively coupled to respective first sets of electrode plates 142', 142" and 142'''. A second passageway 148 is also provided having a metallized inner diameter in order to connect the second set of electrode plates 144 together. The second passageway 148 receives a ground lead 150 therethrough, which is conductively coupled to the conductive inner diameter of the second passageway, all in a manner functionally similar to that described above.

Figure 11:
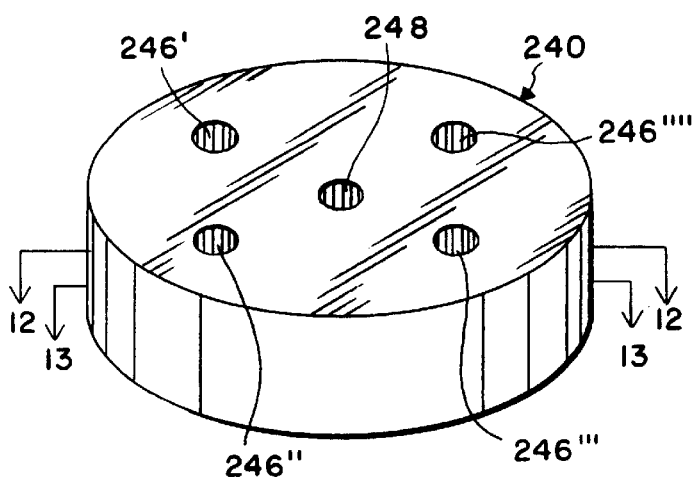
FIG. 11 is a perspective view of an internally grounded quadpolar (discoidal) feedthrough filter capacitor embodying aspects of the present invention.
Figure 12:
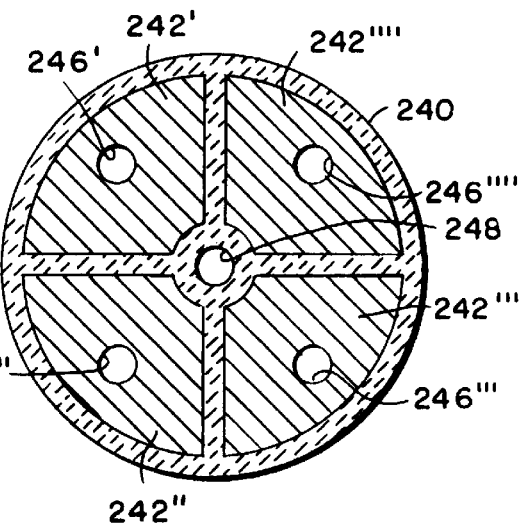
FIG. 12 is a horizontal section taken generally along the line 12—12 of FIG. 11, illustrating four sets of conductive plates embedded within the quadpolar feedthrough filter capacitor.
Figure 13:
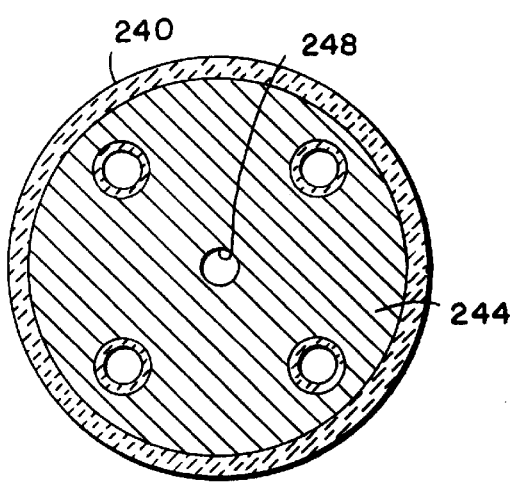
FIG. 13 is a horizontal section taken generally along the line 13—13 of FIG. 11, illustrating the provision of a ground plane within the quadpolar feedthrough filter capacitor.
Figure 15:
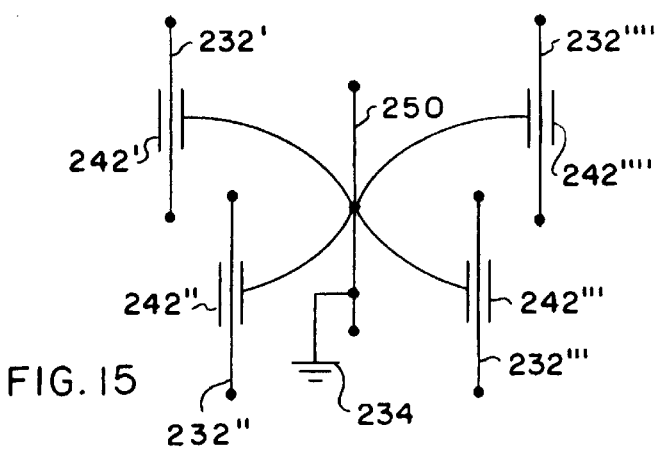
FIG. 15 is an electrical schematic of the assembly shown in FIG. 14.

FIGS. 11–15 illustrate the construction of a third type of feedthrough filter capacitor assembly 230 embodying the present invention. More specifically, the feedthrough filter capacitor assembly 230 utilizes a quadpolar feedthrough filter capacitor 240 wherein the conductive terminal pins 232'–232''' are symmetrically positioned about a central ground pin 250. The overall construction of this particular embodiment of the invention is similar to those described above. FIG. 15 further illustrates an electrical schematic corresponding to the feedthrough filter capacitor assembly 230 of FIG. 14.

Figure 17:
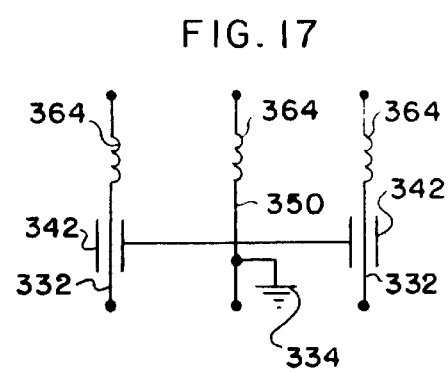
FIG. 17 is an electrical schematic drawing illustrating the improved filtering characteristics of the assembly of FIG. 16 relative to the assembly of FIG. 14.

With reference now to FIGS. 16 and 17, there is illustrated yet another embodiment of a feedthrough filter capacitor assembly 330 embodying the present invention. In this particular embodiment, the conductive ferrule 334, rather than being planar as in the previous embodiments, is cup-shaped so as to receive therein the quadpolar feedthrough filter capacitor 340. The quadpolar feedthrough filter capacitor 340 may be identical to the feedthrough filter capacitor 240 of FIGS. 11–14.

The feedthrough filter capacitor assembly 330 of FIGS. 16 and 17 further includes an optional ferrite bead disc inductor 364 that is positioned immediately adjacent to the feedthrough filter capacitor 340 and within the conductive ferrule 334. An insulative epoxy fill 366 is provided to capture the inductor 364 within the conductive ferrule 334 as shown. The advantage of including the inductor 364 as part of the feedthrough filter capacitor assembly 330 is improved attenuation This is shown by the electrical schematic of FIG. 17.

FIGS. 18–21 illustrate further embodiments of the feedthrough filter capacitor assembly 430 which are similar to that illustrated in FIG. 16, but which utilize a different type of feedthrough filter capacitor 440 that accommodates use of a nail-head lead 450. In particular, the feedthrough filter capacitor 440 includes a metallized pad 468 on an outer surface thereof surrounding the central or second passageway 448. This metallized pad 468 is formed with the metallized inner diameter of the second passageway 448 so that the head 470 of the ground lead 450 may abut against it to ensure a satisfactory conductive connection between the second set of electrode plates 444 (the ground planes) and the ground lead 450. In these embodiments, the ground lead 450 does not extend through the conductive ferrule 434, but rather terminates at the head 470.

The illustrated nail-head lead 450 is merely exemplary of similar equivalent structures wherein the conductive connection between the metallized inner diameter of the second passageway 448 is effected through an abutting connection or the like with the conductive ferrule 434. More specifically, rather than utilizing a nail-head lead 450 as shown in the drawings, the ground lead 450 may be press fitted, cold welded, welded, or brazed to form an electrical and mechanical connection between the ground lead 450 and the conductive ferrule 434. This electrical and mechanical connection between the two components may be at a selected surface location as shown in FIG. 19, or may be within an aperture or passageway provided through the conductive ferrule. An equivalent alternative ground lead 450 includes a flowable nail-head lead wherein the illustrated rigid nail head lead is replaced with a flowable conductive filler material such as solder or a conductive adhesive, which is inserted into the second passageway 448 to make contact with the metallized inner diameter thereof and the underlying surface of conductive ferrule 434.

Other features of the present invention are further illustrated in the embodiments of FIGS. 19–21. In FIG. 19 one of the conductive terminal pins 432 is constructed to include a wire bond pad 472. Further, the conductive ferrule 434 is constructed to include a laser weld "H" flange 474. In the embodiment of FIG. 20, the nail head lead 450 extends upwardly through the inductor 464 to provide a ground pin 476. In FIG. 21, the conductive ferrule 434 includes a segmented planar radial perimeter 478, typically formed as a standard hex head, and adjacent threads 480 for attaching the conductive ferrule 434 to a suitable conductive substrate.

A significant advantage of the novel internally grounded feedthrough capacitor assemblies as described herein is that the mechanical (and electrical) connection to the outside diameter of the capacitor is eliminated. In addition to reducing cost, this has the added effect of greatly reducing the mechanical stresses coupled to the relatively brittle ceramic capacitor structure caused by the mismatch in the thermal coefficient of expansion of the ceramic capacitor and the terminal or substrate to which it is mounted. This is particularly important for medical implant devices where the combined filter capacitor and hermetic terminal see high terminal stresses due to the requirement to weld said structure to the housing of the medical implant device. Thus, the capacitor structure is allowed to mechanically "float" in relative isolation from the surrounding materials.

Another advantage of the internally grounded feedthrough capacitor assemblies as described herein, when installed in conjunction with a hermetic seal terminal, is that by elimination of the mechanical and electrical connection to the outside perimeter or outside diameter, the possibility of an adjunct or false hermetic seal is reduced or eliminated. In the prior art (in particular the feedthrough capacitor described by the '551 patent), the electrical/mechanical connection to the capacitor outside diameter is accomplished with a conductive thermosetting material such as silver filled epoxy or polyamide. This material can mask a leaking or defective hermetic terminal (a long term helium leak test of up to several hours may be able to detect the leak defect, but is in practice impractical and too costly). The elimination of this polymer material is therefore an important benefit.

Another benefit is that the penetration of the internal electrode plates to the external perimeter or outside diameter of the capacitor has been eliminated. This results in a more physically robust capacitor design with less tendency to delaminate along the knitline or internal electrode lamination layer. Accordingly, there will be less tendency for the capacitor to fracture, delaminate or otherwise structurally fail under thermal, mechanical or piezoelectric stresses. The only point of electrode penetration will be the inside diameter of the cylindrical holes for lead connection. This will tend to make the capacitor a more solid, monolithic structure which is more resistant to moisture or solvent penetration.

Although several embodiments of the invention have been described in detail for purposes of illustration, various further modifications may be made without departing from the spirit and scope of the invention. Accordingly, the invention is not to be limited, except as by the appended claims.

We claim:

1. A feedthrough filter capacitor assembly, comprising:
   at least one conductive terminal pin;
   a conductive ferrule through which the terminal pin passes in non-conductive relation;

a feedthrough filter capacitor having first and second sets of electrode plates and a first passageway through which the terminal pin extends in conductive relation with the first set of electrode plates; and a ground lead conductively coupled to the conductive ferrule, and extending into a second passageway through the feedthrough filter capacitor in conductive relation with the second set of electrode plates.

2. The assembly of claim 1, wherein the feedthrough filter capacitor includes non-metallized exterior surfaces.

3. The assembly of claim 1, including an inductor adjacent to the feedthrough filter capacitor, through which the terminal pin extends.

4. The assembly of claim 1, including means for hermetically sealing passage of the terminal pin through the conductive ferrule.

5. The assembly of claim 1, wherein the terminal pin includes a wire bond pad at an end thereof.

6. The assembly of claim 1, wherein the ground lead comprises a nail-head lead having one end that abuts a portion of the conductive ferrule.

7. The assembly of claim 6, wherein the nail-head lead extends from the conductive ferrule, through and beyond the feedthrough filter capacitor to provide a ground pin.

8. The assembly of claim 1, wherein the ground lead comprises a ground pin that extends through the conductive ferrule and the feedthrough filter capacitor.

9. The assembly of claim 8, including means for hermetically sealing passage of the ground lead through the conductive ferrule.

10. The assembly of claim 8, wherein the ground lead comprises a hollow gas back-fill tubelet.

11. A feedthrough filter capacitor assembly utilized in connection with a conductive substrate, comprising:

at least one conductive terminal pin;

means for mounting the terminal pin for passage through an opening formed in the conductive substrate with the terminal pin and the substrate in non-conductive relation;

a feed-through filter capacitor having first and second sets of electrode plates, a first passageway through which the terminal pin extends in conductive relation with the first set of electrode plates, and a second passageway; and a ground lead conductively coupled to the conductive substrate, and extending into the second passageway in conductive relation with the second set of electrode plates.

12. The assembly of claim 11, wherein the feedthrough filter capacitor is asymmetrical.

13. The assembly of claim 11, wherein the feedthrough filter capacitor is symmetrical about the ground lead.

14. The assembly of claim 13, wherein the feedthrough filter capacitor comprises a discoidal capacitor.

15. The assembly of claim 11, wherein the terminal pin mounting means includes means for hermetically sealing passage of the terminal pin through the substrate opening.

16. The assembly of claim 11, wherein the terminal pin mounting means comprises a conductive ferrule adapted for mounting onto the substrate in a position extending through the substrate opening, and insulator means for supporting the terminal pin from the ferrule in electrically insulated relation.

17. The assembly of claim 16, wherein the terminal pin, ferrule and insulator means comprises a prefabricated terminal pin subassembly.

18. The assembly of claim 16, wherein the ground lead comprises a nail-head lead having one end that abuts a portion of the conductive ferrule.

19. The assembly of claim 18, wherein the nail-head lead extends from the conductive ferrule, through and beyond the feedthrough filter capacitor to provide a ground pin.

20. The assembly of claim 16, wherein the conductive ferrule includes a laser weld H flange for attachment to the conductive substrate.

21. The assembly of claim 16, wherein the conductive ferrule includes a segmented planar radial perimeter and threads, for attachment to the conductive substrate.

22. The assembly of claim 11, including an inductor adjacent to the feedthrough filter capacitor through which the terminal pin extends, and wherein the feedthrough filter capacitor includes non-metallized exterior surfaces.

23. The assembly of claim 11, including means for hermetically sealing passage of the terminal pin through the conductive substrate.

24. The assembly of claim 11, wherein the ground lead comprises a ground pin that extends through the conductive ferrule and the feedthrough filter capacitor.

25. A feedthrough filter capacitor assembly utilized in connection with a conductive substrate, comprising:

at least one conductive terminal pin;

means for mounting the terminal pin for passage through an opening formed in the conductive substrate with the terminal pin and the substrate in non-conductive relation;

a feed-through filter capacitor having first and second sets of electrode plates, a first passageway through which the terminal pin extends in conductive relation with the first set of electrode plates, and a second passageway, wherein the feedthrough filter capacitor includes non-metallized exterior surfaces;

a ground lead conductively coupled to the conductive substrate, and extending into the second passageway in conductive relation with the second set of electrode plates; and means for hermetically sealing passage of the terminal pin through the terminal pin mounting means.

26. The assembly of claim 25, wherein the terminal pin mounting means comprises a conductive ferrule adapted for mounting onto the substrate in a position extending through the substrate opening, and insulator means for supporting the terminal pin from the ferrule in electrically insulated relation.

27. The assembly of claim 26, wherein the conductive ferrule comprises a receptacle for receiving therein the feedthrough filter capacitor.

28. The assembly of claim 27, including an inductor adjacent to the feedthrough filter capacitor, through which the terminal pin extends.

29. The assembly of claim 28, wherein the inductor is a ferrite bead disc positioned within the conductive ferrule and captured by an insulative epoxy fill.

* * * * *